United States Patent [19]
Maidonis et al.

[11] Patent Number: 5,962,687
[45] Date of Patent: Oct. 5, 1999

[54] METHOD FOR THE PRODUCTION OF MAGNESIUM PYRIDOXAL-5'-PHOSPHATE GLUTAMATE AND INTERMEDIATE PRODUCTS OBTAINED THEREBY

[75] Inventors: Panagiotis Maidonis, Darmstadt; Werner Schneider, Kolbenz, both of Germany

[73] Assignee: Steigerwald Arzneimittelwerk GmbH, Darmstadt, Germany

[21] Appl. No.: 09/029,426

[22] PCT Filed: Aug. 26, 1996

[86] PCT No.: PCT/EP96/03749

§ 371 Date: Jun. 29, 1998

§ 102(e) Date: Jun. 29, 1998

[87] PCT Pub. No.: WO97/09334

PCT Pub. Date: Mar. 13, 1997

[30] Foreign Application Priority Data

Sep. 4, 1995 [DE] Germany .......................... 195 32 625

[51] Int. Cl.⁶ .............................. C07F 9/58; C07D 213/66
[52] U.S. Cl. .............................................. 546/24; 546/298
[58] Field of Search ....................... 546/24, 298

[56] References Cited

U.S. PATENT DOCUMENTS 3,663,557  5/1972  Forget ........................................ 546/22

FOREIGN PATENT DOCUMENTS 24 62742    7/1976   Germany .
401 16963  11/1991   Germany .

OTHER PUBLICATIONS

Iwanami et al., "A New Synthesis of Pyridoxial–5–Phospate," Bull. Chem. Soc. Japan (1968), vol. 41 (1) 161–165.
Chemical Abstracts 96; 52138 (1981).
Chemical Abstracts 86: 16550 (1977).
Chemical Abstracts 101; 007040 (1984).
Chemical Abstracts 67; 802109 (1967).

Primary Examiner—Alan L. Rotman
Attorney, Agent, or Firm—Fitch, Even, Tabin & Flannery

[57] ABSTRACT

The invention relates to a method for the production of magnesium pyridoxal-5'-phosphate glutamate, in which pyridoxine or an acid addition salt thereof is oxidised with manganese (IV) oxide to pyridoxal; pyridoxal is reacted with p-phenetidine under formation of the Schiff's base p-phenetidyl-pyridoxal; p-phenedityl-pyridoxal is selectively phosphorylated on the 5'-hydroxymethyl group under formation of p-phenetidyl-pyridoxal-5'-phosphate; p-phenetidyl-pyridoxal-5'-phosphate is hydrolysed under formation of an alkali metal salt of pyridoxal-5'-phosphate; the alkali metal ions are removed in order to obtain pyridoxal-5'-phosphate; pyridoxal-5'-phosphate is reacted with a reaction product of a magnesium alcoholate and L-glutarnic acid; and the formed magnesium pyridoxal-5'-phosphate glutamate is isolated. Furthermore, the invention relates to intermediate products obtained with this method.

10 Claims, No Drawings

METHOD FOR THE PRODUCTION OF MAGNESIUM PYRIDOXAL-5'-PHOSPHATE GLUTAMATE AND INTERMEDIATE PRODUCTS OBTAINED THEREBY

CROSS-REFERENCE

This application is a 371 of PCT/EP96/03749 filed Aug. 26, 1996.

The invention relates to the method for the production of magnesium pyridoxal-5'-phosphate glutamate. The invention especially relates to a new method for the production of magnesium pyridoxal-5'-phosphate glutamate starting from an acid addition salt of pyridoxine, such as pyridoxine hydrochloride, in which pyridoxal-5'-phosphate is obtained as an intermediate product.

Magnesium pyridoxal-5'-phosphate glutamate is known from DE 24 61 742. In this publication, it is proposed as a medicament for prophylaxis and therapy of metabolic disturbances, especially for influencing the lipid and cholesterol state. DE 40 16 963 relates to the use of magnesium pyridoxal-51'-phosphate glutamate for the reduction of LDL-bound peroxides and for prevention of vascular damage.

Considering the importance of magnesium pyridoxal-5'-phosphate glutamate as a medicament, the need exists for a new, simpler and more economic synthesis for this substance. Therefore, an object of the invention is to provide a synthesis of this type.

The object is solved according to the invention by providing a synthesis for magnesium pyridoxal-5'-phosphate glutamate in which pyridoxal-5'-phosphate is obtained as an intermediate product. The pyridoxal-5'-phosphate accumulates in the form of an aqueous solution from which the pyridoxal-5'-phosphate can be isolated if required. However, the obtained pyridoxal-5'-phosphate solution can also be reacted to the end product in an advantageous manner without isolation of the pyridoxal-5'-phosphate. Therewith, the steps required according to the state of the art for purification and drying of the pyridoxal-5'-phosphate are omitted.

A further point of the invention relates to the fact that, starting from pyridoxine, and especially an acid addition salt of pyridoxine, such as pyridoxine hydrochloride, pyridoxal-5'-phosphate is produced in a high yield according to a new method with p-phenetidyl pyridoxal and p-phenetidyl-pyridoxal-5'-phosphate as intermediate products.

Subject matter of the invention is a method for the synthesis of magnesium pyridoxal-5'-phosphate glutamate which is characterised in that:

A) pyridoxine or an acid addition salt thereof is oxidised with manganese(IV) oxide to pyridoxal;

B) pyridoxal is reacted with p-phenetidine under formation of the Schiff's base p-phenetidyl-pyridoxal;

C) p-phenetidyl-pyridoxal is selectively phosphorylated on the 5'-hydroxymethyl group under formation of p-phenetidyl-pyridoxal-5'-phosphate;

D) p-phenetidyl-pyridoxal-5'-phosphate is hydrolysed under formation of an alkali metal salt of pyridoxal-5'-phosphate;

E) the alkali metal ions are removed in order to obtain pyridoxal-5'-phosphate;

F) pyridoxal-5'-phosphate is reacted with a reaction product of a magnesium alcoholate and L-glutamic acid; and G) the formed magnesium pyridoxal-5'-phosphate glutamate is isolated.

A preferred embodiment of the invention is represented in the following reaction scheme.

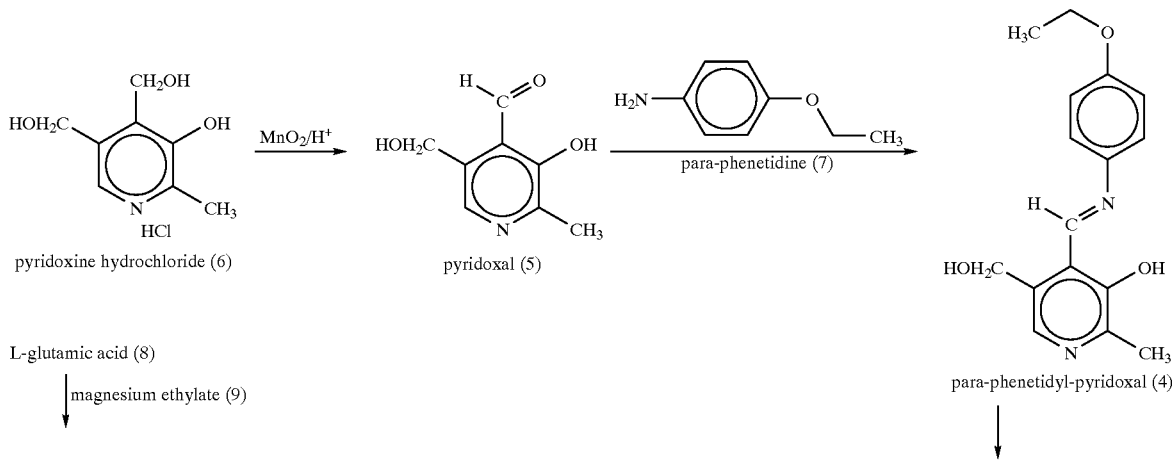

-continued

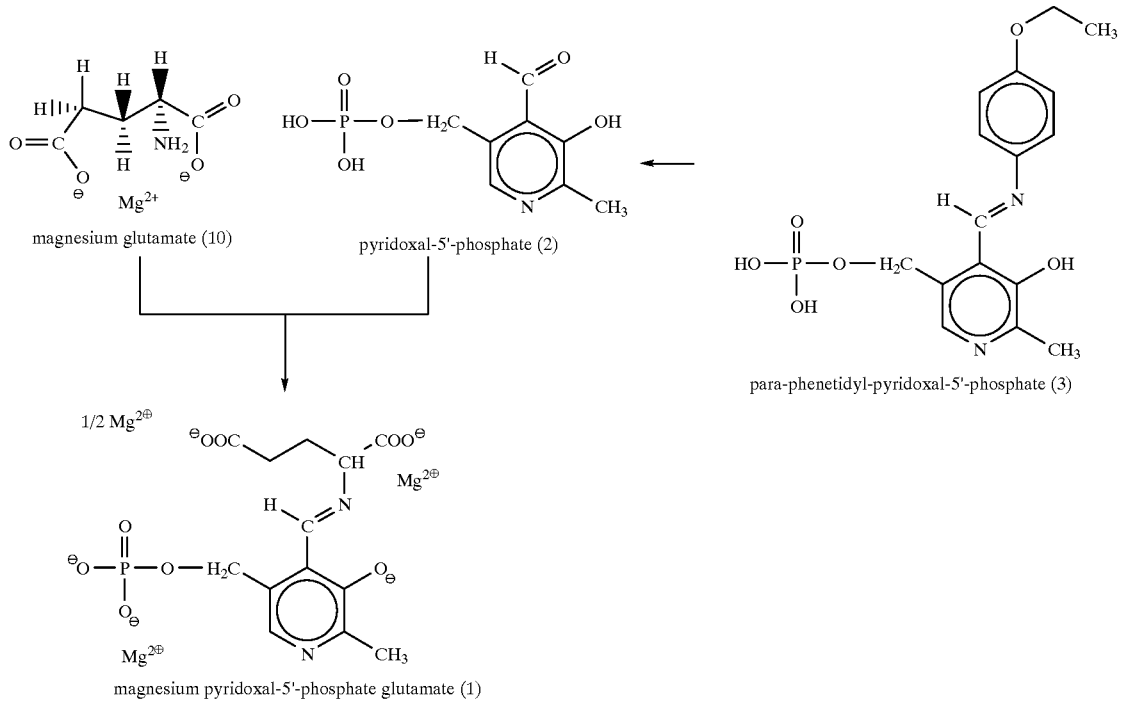

magnesium glutamate (10)

pyridoxal-5'-phosphate (2)

magnesium pyridoxal-5'-phosphate glutamate (1)

para-phenetidyl-pyridoxal-5'-phosphate (3)

Molecular weight of the compounds.

| manganese(IV) oxide | | MnO | 86,9 g/mol |
|---|---|---|---|
| para-phenetidine | (7) | $C_8H_{11}NO$ | 137,0 g/mol |
| para-phenetidyl-pyridoxal | (4) | $C_{16}H_{18}N_2O_3$ | 286,0 g/mol |
| para-phenetidyl-pyridoxal-5'-phosphate | (3) | $C_{16}H_{19}N_2O_6P$ | 366,0 g/mol |
| pyridoxal | (5) | $C_8H_9NO_3$ | 167,0 g/mol |
| pyridoxal-5'-phosphate | (2) | $C_8H_{10}NO_6P$ | 247,0 g/mol |
| pyridoxal-5'-phosphate monohydrate | (2') | $C_8H_{12}NO_7P$ | 265,0 g/mol |
| pyridoxine hydrochloride | (6) | $C_8H_{12}ClNO_3$ | 205,5 g/mol |
| magnesium pyridoxal-5'-phosphate glutamate | (1) | $C_3H_{11}Mg_{2.5}N_2O_9P$ | 432,0 g/mol |
| magnesium pyridoxal-5'-phosphate glutamate dihydrate | (1') | $C_{13}H_{15}Mg_{2.5}N_2O_{11}P$ | 464,0 g/mol |

It has been shown to be advantageous to carry out the individual synthesis steps discontinuously in suitable temperature and pH controlled units under light and/or air exclusion.

In order to be able to monitor the chemical reaction at any time, it is possible to carry out in-process controls for example. In-process controls of this type can comprise analyses, such as HPLC analyses, which can be reliably carried out in a short amount of time (15 min).

Furthermore, it has been shown to be suitable to release the product of each step for further processing first after carrying out an analysis and a purity test.

The individual steps of the synthesis are illustrated in detail in the following.

According to the invention, pyridoxine, preferably in form of an acid addition salt such as pyridoxine hydrochloride (6), is first oxidised to pyridoxal (5). A suitable oxidation agent is manganese(IV) oxide which is suitably used in activated form. The oxidation is then preferably carried out in sulfuric acid solution under controlled pH and temperature conditions as well as under light exclusion. The degree of reaction can be continuously examined by means of a suitable analytical system (for example, HPLC). It is particularly preferred to stop the reaction as soon as the entire amount of pyridoxine was oxidised. As opposed to known methods of oxidation of pyridoxine hydrochloride (6), the amount of oxidation side products formed can be diminished and the yield of pyridoxal (5) can be increased thereby.

The described oxidation of a pyridoxine acid addition salt to pyridoxal (5) with manganese(IV) oxide is typically carried out in the acidic range without adherence to particular pH or temperature conditions. However, oxidation with manganese(IV) oxide is carried out in a particularly advantageous manner at a constant pH value of 5,1 and a constant temperature of 14° C. for further increasing the yield and minimising the amount of side products formed.

The reaction mixture can subsequently be subjected to processing for separation, for example by filtration, of precipitated material such as reacted or non-reacted oxidation agent, for example manganese salts. Thereby, it is also possible to recover non-reacted oxidation agent, such as manganese(IV) oxide and newly add this later to the process.

Isolation of pyridoxal (5) can be carried out by the person skilled in the art according to new methods without difficulty.

However, according to the invention, isolation is not required and the obtained pyridoxal solution can be directly used as an aqueous pyridoxal solution in the next reaction step.

An aqueous solution of pyridoxal (5), preferably relating to the reaction solution obtained in the oxidation, is brought to a weakly acidic pH value and preferably a pH value of 4.5. After that, p-phenetidine (7) is added preferably in slight excess. After conclusion of the reaction, the formed precipitate is separated (preferably filtered), for example by washing with water and/or an organic solvent, purified, and preferably dried, whereby p-phenetidyl-pyridoxal (4) is obtained.

Excess p-phenetidine (7) can be recovered. If ions originating from the oxidation agent, such as manganese(II) ions, are contained in the solution obtained after the separation of the precipitate, these can also be recovered by precipitation with the aid of lye for example.

The Schiff's base p-phenetidyl-pyridoxal (4) is subjected to a treatment for selective phosphorylation at the 5'-hydroxymethyl group under formation of p-phenetidyl-pyridoxal 5'-phosphate (3). The phosphorylation occurs through treating p-phenetidyl-pyridoxal (4) with a suitable phosphorylation agent. For example, reaction with polyphosphoric acid is suitable.

In this case, phosphorylation preferably occurs under controlled temperature conditions (4 to 25° C.) as well as light exclusion. For an optimal reaction course, it has been shown to be favourable to bring the dried p-phenetidyl-pyridoxal (4) to a particle size of $\leqq 500$ μm before the reaction. Furthermore, it is advantageous to mix p-phenetidyl-pyridoxal (4) and polyphosphoric acid as intimately as possible for reaction, for example in a kneading unit. The degree of reaction can be constantly examined by means of a suitable analytical system (for example, HPLC). It is particularly preferred to stop the reaction as soon as the entire amount of p-phenetidyl-pyridoxal (4) is phosphorated.

According to a particularly preferred embodiment, polyphosphoric acid and p-phenetidyl-pyridoxal are used in the ratio of 4–6 parts to 1 part.

In the above described reaction, p-phenetidyl-pyridoxal-5'-polyphosphates form. Then, through the subsequent addition of water and acid, a partial hydrolysis occurs under formation and precipitation of p-phenetidyl-pyridoxal-5'-phosphate (3). The precipitation can be promoted by addition of lye. The compound obtained is purified in the customary manner, for example by washing with water and/or an organic solvent. It can be dried and isolated, but is suitably processed as a moist precipitate for the purpose of further synthesis.

The phosphate accumulating due to the excess of polyphosphate can be reacted with calcium hydroxide to calcium phosphate and can be optionally easily stored with low risk and/or further processed or disposed.

p-phenetidyl-pyridoxal-5'-phosphate (3) is then hydrolysed to pyridoxal 5'-phosphate (2) and p-phenetidine (7) by treatment with an aqueous alkali solution, preferably at a pH value of more than 12.5. The formed p-phenetidine and the alkali metal salt of pyridoxal 5'-phosphate can be separated according to any suitable method. p-phenetidine (7) can be separated from the aqueous solution by extraction with a suitable organic solvent, for example an aliphatic or aromatic hydrocarbon such as toluol.

Alternatively, the p-phenetidine (7) can be separated according to a preferable embodiment by means of a liquid-liquid separator unit. A separation of this type is more time-saving, more ecological, more efficient, easier and therewith more economic than the extraction.

The p-phenetidine (7) recovered in this reaction step can be purified by means of distillation for example and then newly used in the first reaction step.

The alkali metal salt of pyridoxal-5'-phosphate (2) can be precipitated from the obtained aqueous solution by concentration. The precipitate can be further purified by washing or recrystallization for example.

In order to produce magnesium pyridoxal-5'-phosphate glutamate (1) from the alkali metal salt of pyridoxal-5'-phosphate (2), the alkali metal ions must first be removed. For this purpose, any suitable method can be employed. For example, the obtained aqueous alkali metal salt solution of pyridoxal-5'-phosphate can be subjected to an ion exchange treatment. The solution obtained thereby can —after optional concentration—be directly used for synthesis of magnesium pyridoxal-5'-phosphate glutamate (1). It is also possible to isolate free pyridoxal-5'-phosphate (2) from the aqueous solution and to purify the compound according to customary methods known to the person skilled in the art. For the next synthesis step, an aqueous solution of previously isolated and purified pyridoxal -5'-phosphate (2) can be used in this case.

The aqueous solution of pyridoxal-5'-phosphate (2) is added to a solution which was obtained by reaction of a magnesium alkholate with water and addition of glutamic acid (8). magnesium ethylate (9) is particularly preferred as a magnesium alcoholate because ethanol is then released by the reaction which does not encumber the pharmaceutical quality of the produced active ingredient with any undesired residues. The mixture is then added to a suitable solvent, preferably ethanol. The reaction is preferably carried out in the cold under air and light exclusion in as much as this is conducive to no side products forming. Magnesium pyridoxal-5'-phosphate glutamate (1) can be separated from the suspension by filtration for example. The product obtained in this manner can be purified by washing and/or recrystallization and subsequently dried.

By using magnesium ethylate and ethanol, a solution is obtained after separation of magnesium pyridoxal-5'-phosphate glutamate (1) which consists of water and ethanol. The solution can be simply disposed of or can be separated by distillation into its components.

In the following, the invention is illustrated further by an example. In this example, the synthesis of magnesium pyridoxal-5'-phosphate glutamate (1) occurs with the aid of the following equipment:

a) temperature controlled mixing vessel (0 to 100° C.) with pH monitoring and metering unit;

b) temperature controlled kneading unit (0 to 100° C.) with strong gearing in the low rotational speed range;

c) extraction unit (aqueous/organic) and/or liquid-liquid separator;

d) cation exchanger unit;

e) filtration unit and/or solid-liquid separator; and f) drying unit.

HPLC analyses were conducted under the following conditions:

HPLC Conditions

1. System a) chromatographic system:

Shimadzu-unit comprising: LC-10AS liquid chromatograph; SIL-10A Auto Injector; SPD-10AV (UV-VIS; spectrophotometric detector); CBM-10A Communications Bus Module; CLASS-LC10 Software; PC 486, 40 Mhz; Desk Jet 560 C Hewlett Packard.

Stationary Phase (column)

Hypersil ODS 5 μm 250×4.6 mm with pre-column cartridge 20×4.6 mm
Mobile Phase (eluent)
aqueous 0.001 m $KH_2PO_4$ solution with $H_3PO_4$ adjusted to pH=3.

| flow | 1.5 ml/min |
|---|---|
| injection | 5 μl |
| detection | 295 nm |
| analytical time | 15 min | b) preparation: a small (for example drop-size) residual amount of a similar size as possible from the reaction mixture (for example two drops with liquid) is dissolved in five drops 10% sulfuric acid.
HPLC conditions
2. System
a) chromatographic system:
Shimadzu-unit comprising: LC-10AS liquid chromatograph; SIL-10A Auto Injector; SPD-10AV (UV-VIS; spectrophotometric detector); CBM-10A Communications Bus Module; CLASS-LC10Software; PC 486, 40 Mhz; Desk Jet 560 C Hewlett Packard.
Stationary Phase (column)
Hypersil ODS 5μm 250×4.6 mm with pre-column cartridge 20×4.6 mm
Mobile Phase (eluent): 5% B
A=aqueous 0.001 M $KH_2PO_4$ solution with $H_3PO_4$ adjusted to pH=3.
B=acentonitrile

| flow | 1.5 ml/min |
|---|---|
| injection | 5 μl |
| detection | 295 nm |
| analytical time | 10 min | b) preparation: a small (for example drop-size) residual amount of a similar size as possible from the reaction mixture (for example two drops with liquid) is dissolved in five drops 10% sulfuric acid.

PRODUCTION EXAMPLE

1st Step
Production of p-phenetidyl-pyridoxal (4) from pyridoxine hydrochloride (6)
100 g pyridoxine hydrochloride (6) are dissolved in 1500 g water and adjusted to a pH of 5.10 with cold 4N sodium hydroxide solution. The obtained solution is brought to a temperature of 14° C. and added to 75 g activated manganese(IV) oxide under strong stirring.
The reaction starts immediately after manganese dioxide addition and the pH value increases if it is not permanently adjusted. Through addition of 100% sulfuric acid in portions, the pH value of the reaction suspension is held constant at 5.10±0.10 by means of a constant pH constant holder under intensive stirring and temperature control (14±2° C.). The course of the reaction is followed by means of HPLC (system 1) in the form of in-process controls. After approximately ten hours, the entire amount of pyridoxine hydrochloride was converted into pyridoxal. After that, the excess manganese dioxide—non-reacted and contaminated with pyridoxal—is filtered, washed three times with approximately 300 g deionized water and dried at 120° C. 25 g of manganese dioxide is recovered which can be used again. The combined aqueous solutions are first subjected to a membrane filtration (0.8 μm) and then adjusted to pH 4.5 with 10% sulfuric acid. Then, 80 g freshly distilled para-phenetidine is added in a portion to the pyridoxal solution under very intensive stirring. Thereby, the pH value of the reaction mixture increases to about 4.7 and the reaction product abruptly precipitates. This is further stirred for half an hour and subsequently filtered. The para-phenetidine containing therein is recovered by means of a liquid-liquid separator from the filtrate which is to be disposed.
The precipitate is suspended three times each in 700 g deionized water and filtered. Subsequently, it is suspended and filtered by means of an Ultra-Turax in 700 g n-heptane. The n-heptane filtrate is redistilled and the collected para-phenetidine residues are stored until conclusion of the third step.
The residue obtained in this manner is dried at 120° C. and sifted to a particle size of ≦500 μm. 124.8 g (=89.7% theoretical yield) of a fine, very light orange-yellow powder of para-phenetidyl-pyridoxal (4) is obtained.
2nd Step
Production of para-phenetidyl-pyridoxal-5'-phosphate (3) from para-phenetidyl-pyridoxal (4).
1000 g of Polyphosphoric acid are placed into a temperature controlled kneading unit and cooled to 10° C. 250 g para-phenetidyl-pyridoxal (4) are slowly applied in small portions to the Polyphosphoric acid under intensive cooling. The Schiff's base of the pyridoxal slowly dissolves in the phosphorylation reagent under red coloration. The reaction heat formed thereby must be intensively carried off in such a manner that the temperature of the reaction mixture does not exceed 25° C. A temperature increase to about the double of this leads to approximately 20% additional loss of yield. After the entire para-phenetidyl-pyridoxal mass was applied, the reaction mixture is further stirred under intensive cooling (≦25° C.) overnight. On the following day, no more para-phenetidyl-pyridoxal is to be identified by means of an in-process control with the aid of HPLC (system 1). The phosphorylation step is concluded therewith. Subsequently, approximately 2125 g ice are added into the mixing chamber and the reaction suspension is stirred further under intensive cooling for three hours. A homogeneous mustard-coloured mass forms while doing so. It is slowly added to 75 g 95–97% cold sulfuric acid, homogenised and heated for approximately 30 min at 80° C., wherein the polyphosphates are hydrolysed. The hydrolysis is followed by means HPLC (system 2), whereby the exact moment of the stop of hydrolysis is recognised (based on the complete disappearance of the Polyphosphate peak). The end of hydrolysis is brought about by rapid cooling of the reaction solution to 10° C. Thereby, the phosphorylated product begins to precipitate. Then, approximately 7500 g of 2N sodium hydroxide solution pre-cooled to approximately 10° C. are slowly added under intense stirring and cooling until the pH value of the reaction suspension is 2.10. The orange-brown reaction product precipitated thereby is filtered well and washed three times each with approximately 500 g deionized water. The well filtered precipitate is directly used for the third step of the synthesis.
Nevertheless, should the product of this step be dried, this can occur at 105° C. 263.4 g (=82.3% theoretical yield) of an orange-brown fine powder of para-phenetidyl-pyridoxal-5'-phosphate (3) would be obtained.

3rd Step
Production of pyridoxal-5'-phosphate (2) from para-phenetidyl-pyridoxal-5'-phosphate (3).
100 g and/or the corresponding amount of the moist precipitate of para-phenetidyl-pyridoxal-5'-phosphate (3) obtained in the second step are added to 700 g 2N sodium hydroxide solution. The Schiff's base is hydrolysed to pyridoxal-5'-phosphate and para-phenetidyl at pH ≧12.5. In the case that the above given amount of lye is not sufficient in order to obtain a pH ≧12.5—on account of the moist precipitate —the necessary amount of additional 2N sodium hydroxide solution is used. By extracting three times each with 300 g toluol, the para-phenetidine is removed from the solution. The toluol solution is redistilled. As an alternative to toluol extraction, an organic-aqueous-separator for continuous operation can be used for the separation of para-phenetidine. The collected para-phenetidine residues from the first and third steps can be purified by means of distillation and newly used.

The pyridoxal-5'-phosphate is present at the end of this separation operation as a sodium salt in the aqueous solution. By means of 800 ml cation exchanger, for example Amperlite Type IR-120 (1.9 mVal/ml), the sodium ion is removed from pyridoxal-5'-phosphate. A pure aqueous solution of pyridoxal-5'-phosphate is obtained. 2500 ml eluate contain 57–63 g (78.6–86.9% theoretical yield) pyridoxal-$5^1$-phosphate (2). This is concentrated under vacuum at max. 40° C. to approximately 500 ml and used for MPPG production. The Pyridoxal-5'-phosphate synthesised in this manner can also be isolated at this point (new synthesis of pyridoxal-5'-phosphate).

4th Step
Production of magnesium pyridoxal-5'-phosphate glutamate (1) from pyridoxal-5'-phosphate (2).

540 g deionized water are placed into a reaction vessel and cooled to 0–3° C. Under nitrogen atmosphere and light exclusion, 62.58 g magnesium ethylate (9) are added and brought into solution by stirring. Thereby, the temperature increases to approximately 10° C. This is cooled to 3° C., 31.85 g glutamic acid (8) are added, and this is stirred for a further 10 min.

Then, 500 ml pyridoxal-5'-phosphate solution of the third step (≡11.6% solution) is added in small portions within 60–90 min. to the magnesium glutamate solution just produced. Thereby, attention is paid that the pH value of the solution remains within the range 8–9. Subsequently, this is further stirred for 3–5 hours and the resulting solution is filtered.

2000 ml ethanol is placed into a mixing vessel and cooled to 0° C. under nitrogen atmosphere and light exclusion. Subsequently, the solution produced above is added dropwise under stirring. The suspension attained in this manner is further stirred for approximately 15 hours, then filtered, and washed with a total of 200 ml ethanol. After that, the entire product is suspended in approximately 100 ml ethanol and newly filtered. The ethanol-moist product is dried in a drying cabinet at max. 60° C. 94.5–99.5 g (94–99% theoretical yield) of magnesium pyridoxal-5'-phosphate glutamate (1) is obtained.

We claim:
1. A method for the production of magnesium pyridoxal-5'-phosphate glutamate comprising:

A) oxidizing pyridoxine or an acid addition salt thereof with manganese(IV) oxide to pyridoxal;
B) reacting pyridoxal with p-phenetidiene to form p-phenetidyl-pyridoxal;
C) phosphorylating p-phenetidyl-pyridoxal to form p-phenetidyl-pyridoxal-5'-phosphate;
D) hydrolyzing p-phenetidyl-pyridoxal-5'-phosphate to form an alkali metal salt of pyridoxal-5'-phosphate;
E) removing the alkali metal ions to obtain pyridoxal-5'-phosphate;
F) reacting pyridoxal-5'-phosphate with a reaction product of a magnesium alcoholate and L-glutamic acid; and
G) isolating magnesium pyridoxal-5'-phosphate glutamate.

2. A method according to claim 1, wherein the acid addition salt of pyridoxine used in step A is pyridoxine hydrochloride.

3. A method according to claim 1 wherein the oxidation in step A is carried out with activated manganese(IV) oxide in sulfuric acid solution at a pH value of about 5.1 and a constant temperature of about 14° C.

4. A method according to claim 1 wherein a pyridoxal containing reaction solution of the oxidation in step A is used in step B.

5. A method according to claim 1 wherein the phosphorylation in step C is carried out by reaction of p-phenetidyl-pyridoxal with polyphosphoric acid.

6. A method according to claim 5, wherein polyphosphoric acid and p-phenetidyl-pyridoxal are used in a ratio of about 4 parts polyphosphoric acid to about 1 part p-phenetidyl-pyridoxal.

7. A method according to claim 1 wherein an alkali hydroxide is added at step D in an amount effective for hydrolyzing p-phenetidyl-pyridoxal.

8. A method according to claim 1 wherein the alkali metal ions in step E are removed by an ion exchanger.

9. A method according to claim 1 wherein the magnesium alcoholate in step F is magnesium ethylate.

10. A method for the production of pyridoxal-5'-phosphate comprising:

A) oxidizing pyridoxine or an acid addition salt thereof with manganese(IV) oxide to pyridoxal;
B) reacting pyridoxal with p-phenetidiene to form p-phenetidyl-pyridoxal;
C) phosphorylating p-phenetidyl-pyridoxal to form p-phenetidyl-pyridoxal-5'-phosphate;
D) hydrolyzing p-phenetidyl-pyridoxal-5'-phosphate to form an alkali metal salt of pyridoxal-5'-phosphate;
E) removing the alkali metal ions to obtain pridoxal-5'-phosphate;
F) isolating and drying the pyridoxal-5'-phosphate obtained in step E.

* * * * *